United States Patent [19]

Unsell

[11] Patent Number: 5,347,657
[45] Date of Patent: Sep. 20, 1994

[54] SWIM SUIT BOTTOM

[76] Inventor: Robert D. Unsell, 2135 Gentian Rd., Venice, Fla. 34293

[21] Appl. No.: 148,397

[22] Filed: Nov. 8, 1993

[51] Int. Cl.$^5$ ............................................. A41D 5/00
[52] U.S. Cl. ................................................ 2/67; 2/400; 2/401; 2/406; 2/237; 2/255; 2/309
[58] Field of Search ...................... 2/67, 400, 401, 406, 2/236, 237, 238, 255, 256, 257, 258, 259, 260, 260.1, 264, 309; 450/81, 86, 107, 109, 112, 143

[56] References Cited

U.S. PATENT DOCUMENTS

| | | |
|---|---|---|
| D. 275,524 | 9/1984 | Dost . |
| D. 286,100 | 10/1986 | Sawicki . |
| 2,534,934 | 12/1950 | Viniegra ................................... 2/67 |
| 2,675,551 | 4/1954 | Ser Vaas . |
| 2,709,812 | 6/1955 | Kanzow . |
| 3,276,449 | 10/1966 | Morgan .................................. 450/81 |
| 3,280,818 | 10/1966 | Pankey et al. . |
| 3,339,208 | 9/1967 | Marbach . |
| 3,654,630 | 4/1972 | Block . |
| 3,774,241 | 11/1973 | Zerkle . |
| 4,121,305 | 10/1978 | Kolker .................................. 2/406 |
| 4,394,781 | 7/1983 | Axmann . |
| 4,501,024 | 2/1985 | Russo . |
| 4,982,450 | 1/1991 | D'Huissier ............................ 450/81 |

FOREIGN PATENT DOCUMENTS 2481893 11/1981 France ....................................... 2/67

Primary Examiner—Clifford D. Crowder
Assistant Examiner—Gloria Hale
Attorney, Agent, or Firm—Charles J. Prescott

[57] ABSTRACT

A swim suit bottom for both genders having a unique attachment of each end thereof to the user. The swim suit bottom is formed into a single flexible fabric cover having a narrow mid section sized to cover the crotch area and widening at either end thereof to define a front and a back panel. When fully extended over the user in an in-use position, the front panel covers essentially the pubic area and the back panel covers a central buttocks area of the user. The back panel is supported in position by a slender resilient arcuate band which only partially encircles and biasingly engages against the lower torso, extending across the lower back, up around the right and left iliac crests and diagonally downward toward, but not to, the stomach and pubic area. The front panel is held in position by a strip of replaceable double-sided adhesive tape adhered adjacent the end margin of the front panel and then across the skin of the upper pubic area below the stomach. Alternately, a liquid surgical cement may be used for this releasable adhesion. A bathing suit top having two triangular flexible fabric panels and held in position over a female breast area by a combination of a flexible neck strap and replaceable double-sided adhesive tape is also provided.

14 Claims, 2 Drawing Sheets

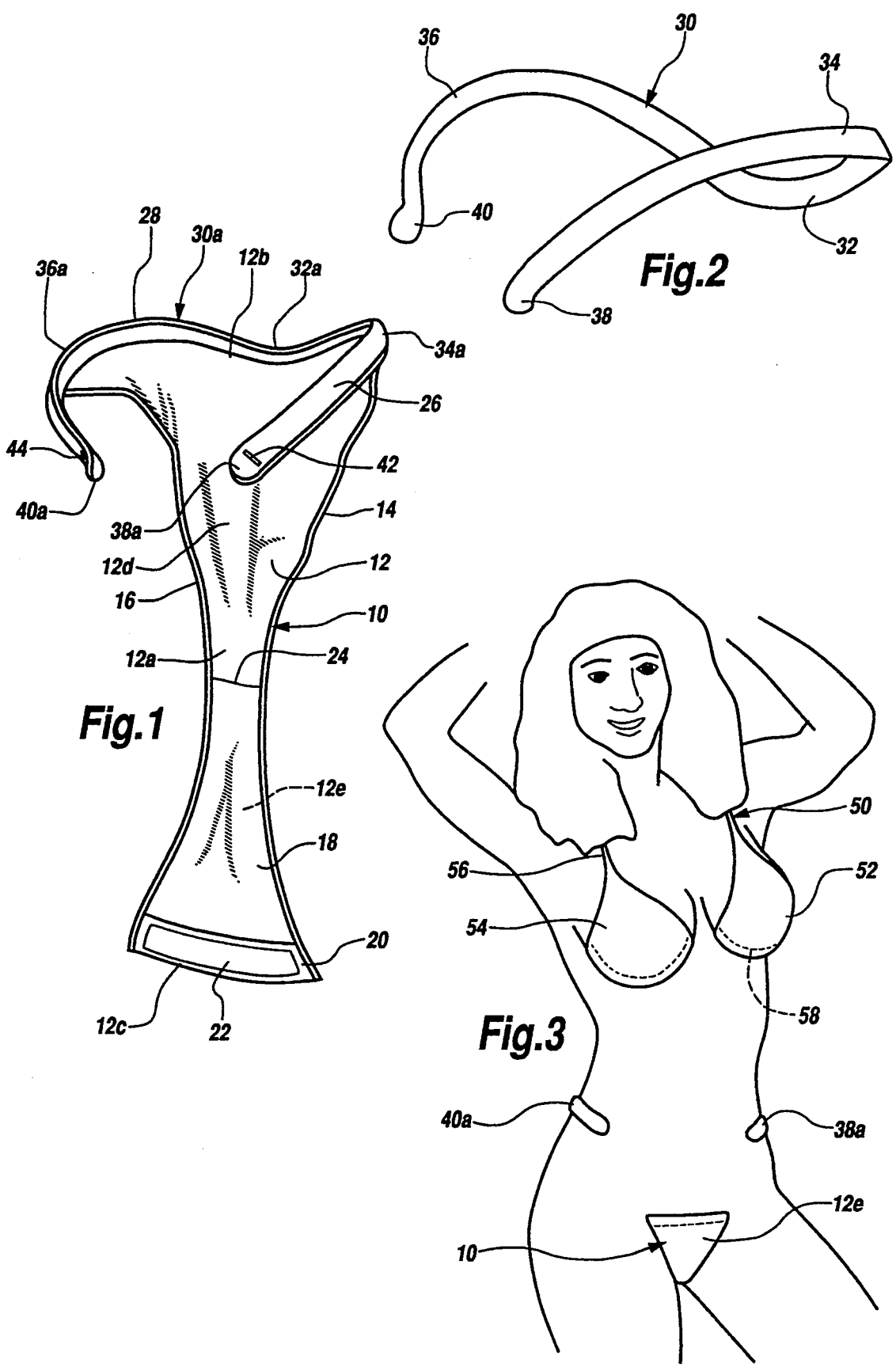

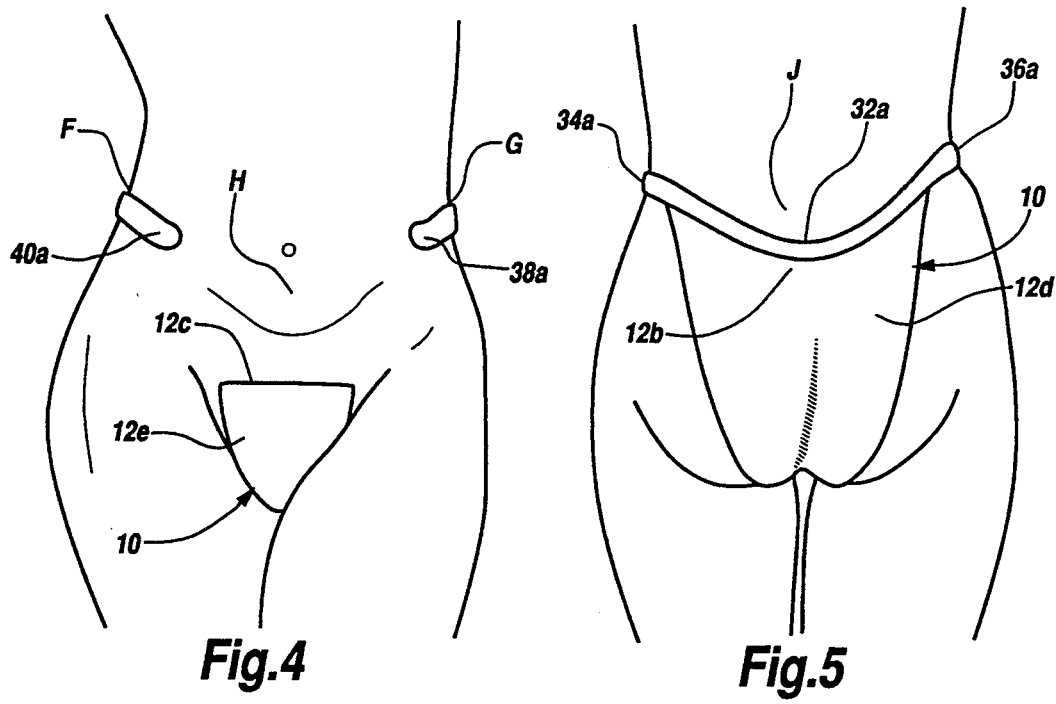
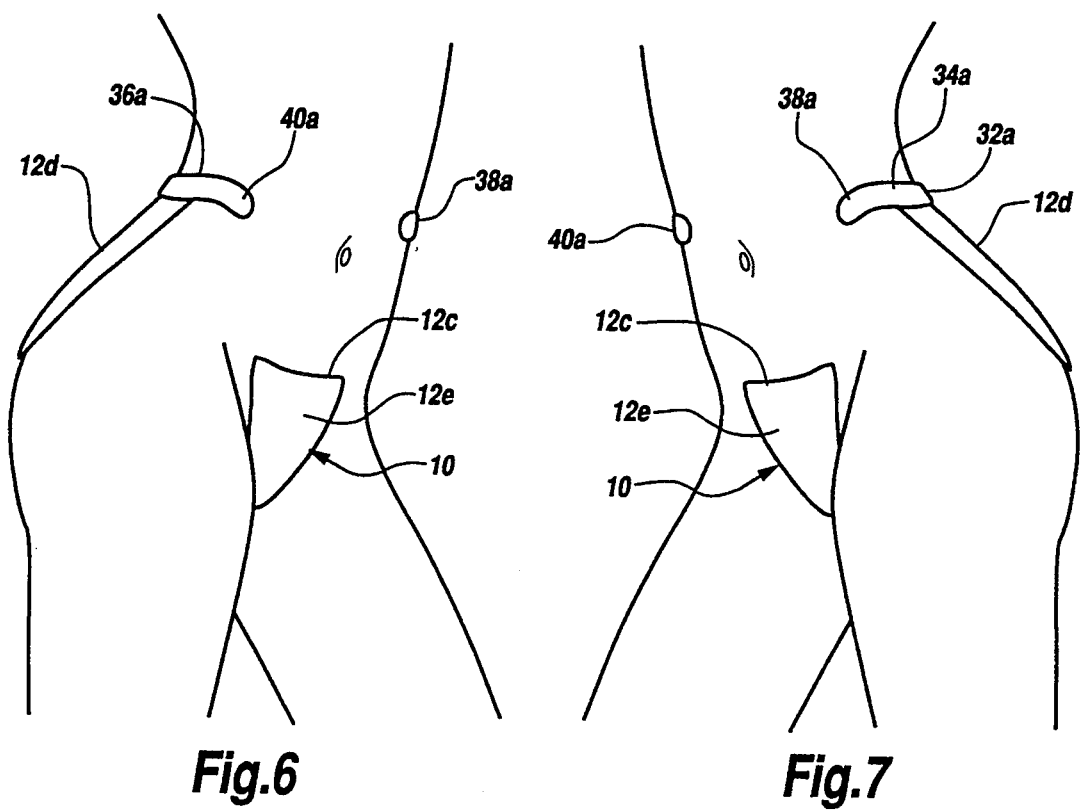

SWIM SUIT BOTTOM

BACKGROUND OF THE INVENTION

1. Scope of Invention

This invention relates generally to swim suits, and more particularly to a swim suit bottom which covers only the pubic area and central buttocks area of the user.

2. Prior Art

Our society has long since moved from swimming suit garments which cover a considerably larger area than normal modesty might require. Thus, the surface skin area which swimming suits now cover has typically diminished considerably to both enhance and increase the level of sun tanning and also to increase individuality of physical expression without going beyond the bounds of either moral or legal decency.

Certainly the two-piece or "Bikini" bathing suits for women represented a step in that direction. More recently, the introduction of the "T-back" bathing suit bottom for women drastically reduced the skin surface area covered down to a very minimal central buttocks area, the crotch area and the pubic area. However, these "T-backs" were otherwise held in place by conventional hip encircling flexible fabric strapping.

A radical bathing suit bottom for women was disclosed in U.S. Pat. No. 3,339,208 invented by Marbach which disclosed a contoured Iccp of resilient steel wire forming a spring adapted to be placed between the wearers legs. With a flexible fabric enclosure for this spring, this device only concealed the crotch area and the central buttocks area up to the sacrum and upwardly in the front area of the user to conceal only the pubic area. However, this device appears to be quite uncomfortable in use and there is no indication that the device was ever successfully marketed. A similar device is disclosed in U.S. Pat. No. 4,394,781 invented by Axmann which also discloses what appears to be a wire frame structure for a swimming suit bottom as well as a generally similar wire structure for a swimming suit top.

A clever adjustable swim suit and sun suit panty garment was invented by Block as disclosed in U.S. Pat. No. 3,654,630 which teaches the adjustable width of a gathering at each side of the swim suit at the hip to vary the skin coverage of both buttocks and frontal areas thereby. The adjustability is accomplished by wrapping and engaging an appropriately sized flexible cord positioned at the right and left sides to encircle and gather a corresponding right and left hip band of the suit.

Another fairly radical bathing suit bottom has been invented by Russo as disclosed in U.S. Pat. No. 4,501,024. This device is of a somewhat conventional "briefs" nature, with the right and left buttocks or cheeks area of the suit being removed. Two other fashionable bathing suits are disclosed in U.S. Des. 286,100 and U.S. Des. 275,524 and are referenced to disclose the general point originally made concerning the increasing brevity of bathing suit design.

Because the present invention entails the use of double-sided adhesive, the wearing apparel device disclosed in U.S. Pat. No. 3,280,818 invented by Pankney is also referenced. This wearing apparel device appears to include a strip of double-sided adhesive tape or the like which supports two separate generally rigid breast cups by adhesion to the skin at a lower margin of the breasts. No other anchoring means is disclosed.

The invention also envisions a partially encircling resilient arcuate band for supporting the back panel of the invention. For that reason, the invention to Zerkle in U.S. Pat. No. 3,774,241; to Ser Vass in U.S. Pat. No. 2,675,551; and to Kanzaw in U.S. Pat. No. 2,709,812 are also referenced in prior art. All of these devices include body fully encircling hoops or bands, the latter two being elastically biased against the body having overlapping resilient hoop structure for adjustability. However, none of these devices envision only a partially body encircling resilient arcuate band as contemplated by the present invention.

The present invention teaches a swimming suit bottom for both genders which includes a somewhat triangular front panel formed of flexible fabric material and a generally triangular rear panel also formed of flexible fabric material, the two being connected or continuous as by forming same from a single flexible fabric sheet and defining a central mid portion between the front and back panels which is sized to cover the crotch area of the user. The front panel is sized, when fully extended, to primarily cover the pubic area and any desired portion of the lower stomach area, being held in that position by a strip of double-sided adhesive or the like applied directly against the skin. The back panel, when fully extended, covers primarily the central buttocks area and is held in position by a resilient arcuate band which only partially encircles the lower torso for added brevity.

BRIEF SUMMARY OF THE INVENTION

This invention is directed to a swim suit bottom for both genders having a unique attachment of each end thereof to the user. The swim suit bottom is formed into a single flexible fabric cover having a narrow mid section sized to cover the crotch area and widening at either end thereof to define a front and a back panel. When fully extended over the user in an in-use position, the front panel covers essentially the pubic area and the back panel covers a central buttocks area of the user. The back panel is supported in position by a slender resilient arcuate band which only partially encircles and biasingly engages against the lower torso, extending across the lower back, up around the right and left iliac crests and diagonally downward toward, but not to, the stomach and pubic area. The front panel is held in position by a strip of replaceable double-sided adhesive tape or the like adhered adjacent the end margin of the front panel and then across the skin of the upper pubic area below the stomach. A bathing suit top having two triangular flexible fabric panels and held in position over a female breast area by a combination of a flexible neck strap and replaceable double-sided adhesive tape is also provided.

It is therefore an object of this invention to provide a bathing suit bottom which uniquely covers only the pubic area, the crotch area and the central buttocks area of the user.

It is another object of this invention to provide a uniquely configured bathing suit bottom which relies upon both a partially encircling resilient band for holding up the back panel of the suit in combination with a strip of double-sided adhesive tape, liquid surgical adhesive or the like for holding the front panel in place.

It is yet another object of this invention to provide a uniquely configured bathing suit bottom which may be repeatedly held in position each time worn by in part a fresh strip of replaceable double-sided adhesive tape.

It is yet another object of this invention to provide a uniquely configured bathing suit bottom in combination with a uniquely configured bathing suit top for females which only covers the breast areas and is held in position by the combination of a flexible neck strap and double-sided adhesive tape positioned along the lower margins of the breasts for securement thereof.

In accordance with these and other objects which will become apparent hereinafter, the instant invention will now be described with reference to the accompanying drawings.

BRIEF DESCRIPTION OF THE DRAWINGS

FIG. 1 is a perspective view of the invention in an upright relaxed position.

FIG. 2 is a perspective view of a resilient arcuate band as part of the invention shown in FIG. 1.

FIG. 3 is a perspective view of the invention shown in FIG. 1 in use along with a uniquely configured swim suit top of this invention.

FIG. 4 is a front perspective view of a user with the invention of FIG. I in place.

FIG. 5 is a back perspective view of FIG. 4.

FIG. 6 is a right side perspective view of FIG. 4.

FIG. 7 is a left side perspective view of FIG. 4.

DETAILED DESCRIPTION OF THE INVENTION

Referring now to the drawing and particularly to FIGS. 1 and 2, the bathing suit bottom is shown generally at numeral 10 and includes a flexible fabric sheet or cover 12, the fabric preferably being double stretch polyester for both elasticity and comfort. This flexible sheet 12 defines a narrow mid section 12a which extends to a taperingly larger front panel 12e and a taperingly larger back panel 12d, the front panel 12e terminating an end margin 12c while the back panel 12d terminates along end margin 12b. The flexible cover 12 has hemmed side margins 14 and 16 for convenience and strength by stitching there along.

A vinyl strip 20 is connected as by stitching across the end margin 12c. This vinyl strip 20 is generally waterproof and is permanently secured to the front panel 12e as shown in FIG. 1.

A strip of double-sided adhesive 22, preferably hypoallergenic, is then applied atop the vinyl strip 20 in replaceable fashion so that the device 10 may be worn with a fresh double sided adhesive strip 22 at each wearing for maximum adhesion. Alternately, a liquid adhesive such as surgical cement may be used for this releasable connection.

A resilient slender injection molded plastic arcuately formed band 30 is also provided, the band 30, being concealed within the wrapped encasing 26 along margin 12b of the flexible sheet or cover 12. Thus, the band 30 may be formed of any convenient colored molded plastic, the encasing material 26 thus determining the aesthetic appearance thereof and also providing a fabric surface contact against the skin of the user in the region which band 30 will engage as described herebelow.

The band 30 in a general sense is shaped as an incomplete or partial oval which does not completely encircle the torso of the user as described herebelow. Arcuate band 30 again, molded of resilient plastic material or alternately formed of a strip of thermal plastic material such as cellulose acetate wrapped around a suitable mold, has a lower central portion 32 which is contoured to fit the "small" or lumbar region J of the back as best seen in FIG. 5. The arcuately configured side portions 34 and 36 are elevated above central portion 32 so as to conform to the right and left lilac crests or hip bones F and G of the user as best seen in FIG. 4. The band 30 then extends diagonally downward from the lilac crests F and G toward, but not to, the stomach area H or the pubic area in FIG. 4.

Thus, it can be now understood that band 30 is resiliently configured so as to bias against the lumbar and lower back area of the user, gripping and being supported by the lilac crest areas F and G and then only slightly wrapping around the frontal area of the torso with ends 38 and 40 terminating just short of the stomach area and the pubic area of the torso. The ends 38 and 40 are recurred outwardly slightly for comfort and to eliminate any pressure points against the torso at that region and to accommodate a broader range of torso sizes and shapes.

The front panel 12e also includes an inner flexible fabric sheet 18 which serves to double the fabric thickness of the front panel 12e for both moisture containment and for the concealment of the pubic area through increased opaqueness. When stretched into position with the mid section 12a covering the crotch area and enclosed band 30a being positioned around the waist and lower back of the user as previously described, the front panel 12e may be stretched or pulled upwardly by the user so as to properly cover the pubic area. Thereafter, the double-sided adhesive 22 may be engaged against the skin of the user just above or at the upper margin of the pubic area and below the stomach area H.

For convenience, the fabric band cover 26 which encases band 30 is collectively numbered at 30a, 32a, 34a, 36a, 38a and 40a in FIGS. 1 and 3 through 7 as corresponding to the underlying portions of the band 30 when encased or covered by covering 26.

To facilitate removal of the resilient band 30, one or both slits 42 and 44 as seen in FIG. 1 generally in the form of button holes, may be provided within the cover 26 adjacent one or both ends 38a and 40a. At least one of these slits 42 and 44 facilitate removal of the band 30 from the encasing cover 26, facilitated by the elastic nature of the fabric material used. By this arrangement, when band 30 is removed, the entire fabric cover 12 may be laundered and then band 30 being easily reinstalled through these same slits 42 and 44. Although shown on an exterior surface cover 26 for clarity, these slits 42 and/or 44 are preferably formed on an inner surface of the cover 26 for concealment.

In FIG. 3, an additional feature of the invention is there shown in the form of a bathing suit top shown generally at numeral 50. This bathing suit top 50 includes triangular flexible fabric panels 52 and 54 which are interconnected at their apexes by a flexible neck strap 56 which supports the upper ends of these triangular panels 52 and 54. The lower margins of these triangular panels 52 and 54 are secured as by double-sided adhesive strips 56 which interengage the skin along the lower margins of the breasts as shown.

While the instant invention has been shown and described herein in what are conceived to be the most practical and preferred embodiments, it is recognized that departures may be made therefrom within the scope of the invention, which is therefore not to be limited to the details disclosed herein, but is to be afforded the full scope of the claims so as to embrace any and all equivalent apparatus and articles.

What is claimed is:

1. A swim suit bottom comprising:
   a length of flexible fabric material defining a front and a back panel and having a mid section narrower in width than each end margin of said front and said back panel;
   said length of material sized to extend between a user's legs at said mid section and upwardly therefrom, said front and back panels covering a pubic area and a central buttocks area of the user;
   a slender resilient arcuate band connected at a central portion thereof across said end margin of said back panel and sized, when resiliently manually expanded, to biasingly engage around a lower back area and right and left lilac crest area of the user, said band extending forwardly on the user over the right and left lilac crest area toward but not to the pubic area, said band having spaced apart ends and when so positioned on the user, holding said rear panel in position covering the central buttocks area;
   an adhesive means for connection adjacent said end margin of said front panel, said adhesive means also being engagable generally horizontally against the skin of the user along an upper portion of the pubic area for holding said front panel in an upward, extended position over the pubic area.

2. A swim suit bottom as set forth in claim 1, wherein:
   said central portion of said band generally conforms to a small or lumbar region of the lower back of the user;
   a right and left lateral portion of said band conforming to the right and left lilac crest areas of the user, said right and left lateral portions being higher than said central portion and said ends of said band.

3. A swim suit bottom as set forth in claim 2, further comprising:
   inner front panel connected against an inner surface of, and generally coextensive with, said front panel;
   said inner front panel providing additional padding over the pubic and crotch area of the user.

4. A swim suit bottom as set forth in claim 3, further comprising:
   a strip of vinyl water resistant material connected along said end margin of said front panel on an inner surface thereof;
   said adhesive means being a different strip of said adhesive tape being connectable onto said vinyl strip and then against the upper pubic area of the user each time said swim suit bottom is worn.

5. A swim suit bottom as set forth in claim 4, wherein:
   said end margin of said back panel is completely wrapped around and encasing said band for added user comfort and appearance.

6. A swim suit bottom as set forth in claim 5, further comprising:
   a slit formed through said end margin of said back panel transversely to and adjacent one end of said band wherein said band is removable from said back panel for laundering and the like.

7. A swim suit bottom comprising:
   a flexible fabric cover having a front panel and a rear panel and a mid section therebetween, side margins of said front and rear panels tapering inwardly from an end margin of said front and rear panels toward said mid section;
   said mid section sized to cover a crotch area of a user, said front panel sized to cover a pubic area of the user, said back panel sized to cover a central buttocks portion of the user;
   a slender resilient arcuate band connected at a central portion thereof to said end margin of said back panel, said band sized to partially encircle and biasingly engage against a lower torso of the user, said band extending around a lower back area of the torso, over a right and left lilac crest of the torso and diagonally downwardly toward the pubic area and terminating at each end of said band, said band, when so positioned around the torso of the user, supporting said rear panel in position over the central buttocks area;
   an adhesive means connected adjacent said end margin of said front panel for adhesive engagement thereof when said front panel is fully extended over the pubic area, along an upper region of the pubic area to support said front panel.

8. A swim suit bottom as set forth in claim 7, wherein:
   said central portion of said band generally conforms to a small or lumbar region of the lower back of the user;
   a right and left lateral portion of said band conforming to the right and left lilac crest areas of the user, said right and left lateral portions being higher than said central portion and said ends of said band.

9. A swim suit bottom as set forth in claim 8, further comprising:
   an inner front panel connected against an inner surface of, and generally coextensive with, said front panel;
   said inner front panel providing additional padding over the pubic and crotch area of the user.

10. A swim suit bottom as set forth in claim 9, further comprising:
    a strip of vinyl water resistant material connected along said end margin of said front panel on an inner surface thereof;
    a different strip of said adhesive tape being connectable onto said vinyl strip and then against the upper pubic area of the user each time said swim suit bottom is worn.

11. A swim suit bottom as set forth in claim 10, wherein:
    said end margin of said back panel is completely wrapped around and encasing said band for added user comfort and appearance.

12. A swim suit bottom as set forth in claim 11, further comprising:
    a slit formed through said end margin of said back panel transversely to and adjacent one end of said band wherein said band is removable from said back panel for laundering and the like.

13. A combination swim suit top and bottom, said swim suit bottom comprising:
    a length of flexible fabric material defining a front and a back panel and having a mid section narrower in width than each end margin of said front and said back panel;
    said length of material sized to extend between a user's legs at said mid section and upwardly therefrom, said front and back panels covering a pubic area and a central buttocks area of the user;
    a slender resilient arcuate band connected at a central portion thereof across said end margin of said back panel and sized, when resiliently manually expanded, to biasingly engage around a lower back area and right and left iliac crest area of the user, said band extending forwardly on the user over the right and left iliac crest area toward but not to the pubic area, said band having spaced apart ends, and when so positioned on the user, holding said rear panel in position covering the central buttocks area;

an adhesive means for connection adjacent said end margin of said front panel, said adhesive means also being engagable generally horizontally against the skin of the user along an upper portion of the pubic area for holding said front panel in an upward, extended position over the pubic area;

said swimsuit top comprising:

a swim suit top formed of two triangular flexible fabric panels each having a strip of double-sided adhesive sized to be connected along a lower generally horizontal margin of each said triangular panel;

each said triangular panel sized to cover a breast of a female user, each said adhesive strip being attachable along a lower boundary of the breast to retain each said lower margin in position;

an elongated flexible strap connected at each end thereof to an upper apex of each said triangular panel, said strap extending behind the neck of the user for holding said triangular panels in position covering the breasts.

14. A combination swim suit top and bottom, said swim suit bottom comprising:

a flexible fabric cover having a front panel and a rear panel and a mid section therebetween, side margins of said front and rear panels tapering inwardly from an end margin of said front and rear panels toward said mid section;

said mid section sized to cover a crotch area of a user, said front panel sized to cover a pubic area of the user, said back panel sized to cover a central buttocks portion of the user;

a slender resilient arcuate band connected at a central portion thereof to said end margin of said back panel, said band sized to partially encircle and biasingly engage against a lower torso of the user, said band extending around a lower back area of the torso, over a right and left iliac crest of the torso and diagonally downwardly toward the pubic area and terminating at each end of said band, said band, when so positioned around the torso of the user, supporting said rear panel in position over the central buttocks area;

an adhesive means connected adjacent said end margin of said front panel for adhesive engagement thereof when said front panel is fully extended over the pubic area, along an upper region of the pubic area to support said front panel;

said swim suit top comprising:

a swim suit top formed of two triangular flexible fabric panels each having a strip of double-sided adhesive sized to be connected along a lower generally horizontal margin of each said triangular panel;

each said triangular panel sized to cover a breast of a female user, each said adhesive strip being attachable along a lower boundary of the breast to retain each said lower margin in position;

an elongated flexible strap connected at each end thereof to an upper apex of each said triangular panel, said strap extending behind the neck of the user for holding said triangular panels in position covering the breasts.

* * * * *